United States Patent [19]

McCaffrey et al.

[11] Patent Number: 5,707,502

[45] Date of Patent: Jan. 13, 1998

[54] SENSORS FOR MEASURING ANALYTE CONCENTRATIONS AND METHODS OF MAKING SAME

[75] Inventors: Robert McCaffrey, Franklin; Katarina Tkacik, Concord; Brian Holman, Medfield; James Flaherty, Attleboro, all of Mass.; Josef Brown, Salem, N.H.; Peter Edelman, Franklin, Mass.

[73] Assignee: Chiron Diagnostics Corporation, E. Walpole, Mass.

[21] Appl. No.: 680,050

[22] Filed: Jul. 12, 1996

[51] Int. Cl.⁶ .................................................. G01N 27/26
[52] U.S. Cl. .................. 204/403; 204/415; 435/287.1; 435/289.1; 435/817
[58] Field of Search .................. 204/403, 415; 435/288, 291, 817

[56] References Cited

U.S. PATENT DOCUMENTS 5,494,562  2/1996  Maley et al. .......................... 204/403

*Primary Examiner*—Bruce F. Bell
*Attorney, Agent, or Firm*—Arthur S. Morgenstern; Stanley Sacks; Robert P. Blackburn

[57] ABSTRACT

A sensor for measuring a concentration of an analyte in a solution. The sensor comprises a substrate layer, an electrode layer and an immobilized enzyme layer. The sensor further includes an enzyme/polymer layer and/or a hydrophobic layer. The enzyme/polymer layer includes an enzyme disposed within a polymer matrix. The hydrophobic layer is formed from a material that is more hydrophobic than the immobilized enzyme layer material. In certain embodiments, the sensor includes the enzyme/polymer layer and the hydrophobic layer disposed between the enzyme/polymer layer and the immobilized enzyme layer such that the enzyme/polymer layer is disposed along the hydrophobic layer within an area above the immobilized enzyme layer.

72 Claims, 7 Drawing Sheets

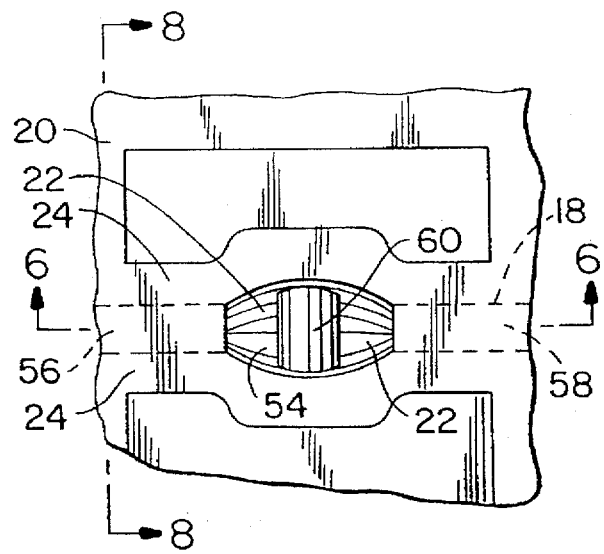
FIG. 5
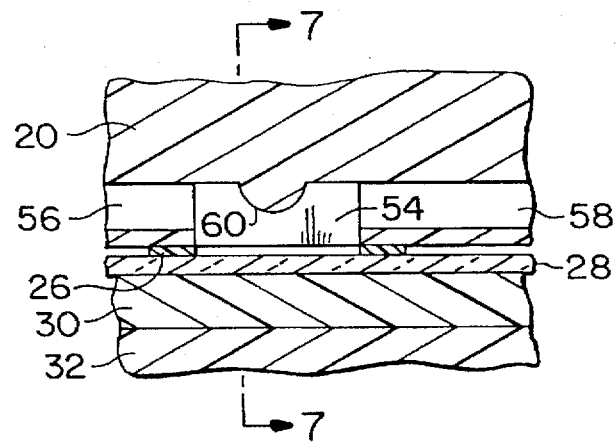
FIG. 6
FIG. 7
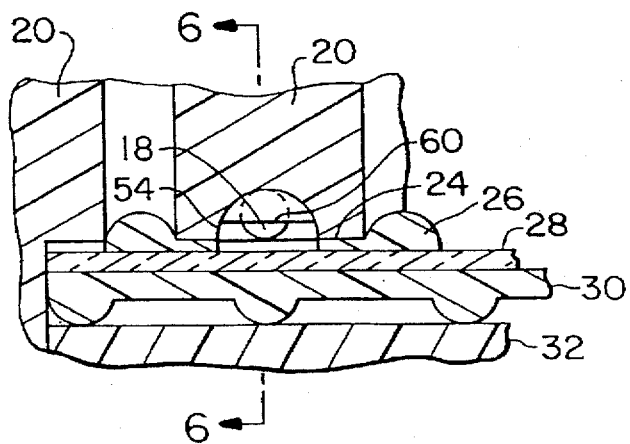
FIG. 8
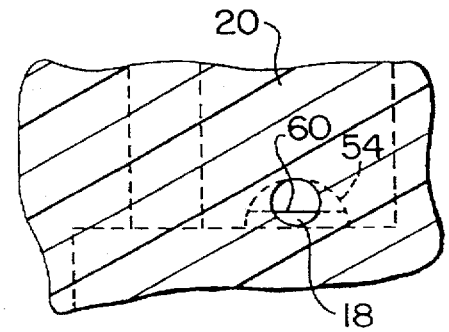

SENSORS FOR MEASURING ANALYTE CONCENTRATIONS AND METHODS OF MAKING SAME

BACKGROUND OF THE INVENTION

1. Field of the Invention

The present invention relates generally to electrochemical sensors and, more particularly, to enzyme catalyzed electrochemical sensors including lactate sensors.

2. Field of the Invention

Under normal conditions, glucose is metabolized to pyruvate which, in turn, is metabolized to carbon dioxide and water with little or no lactate production. Therefore, in a healthy human, the concentration of lactate in blood should be below some critical level. However, if there is a metabolic problem, the level of lactate in the blood may increase above this critical level. In certain systems, it may be desirable to measure the lactate concentration in other biological fluids such as plasma, sweat, tears or urine.

A high level of lactate in blood can indicate a lack of oxygen in the blood resulting from a variety of problems such as circulation shock, a fatal disease with a high mortality rate. Circulation shock occurs when the heart cannot distribute enough blood through the body, and typical causes for this condition are hemorrhaging, dehydration, heart attack, sepsis and certain other infections.

One traditional method of measuring lactate concentrations in blood include reacting lactate with NAD$^+$ to form pyruvate and NADH and subsequently making a spectrophotometric determination of the NADH concentration, which serves as a measure of the lactate concentration. This technique, however, is relatively slow, inefficient and labor intensive.

In a clinical setting, accurate and relatively fast determinations of lactate levels can be determined from blood samples utilizing electrochemical sensors. Conventional sensors are fabricated to be large, comprising many serviceable parts, or small, planar-type sensors which may be more convenient in many circumstances. The term "planar" as used herein refers to the well-known procedure of fabricating a substantially planar structure comprising layers of relatively thin materials, for example, using the well-known thick or thin-film techniques. See, for example, Liu et al., U.S. Pat. No. 4,571,292, and Papadakis et at., U.S. Pat. No. 4,536,274, both of which are incorporated herein by reference.

In the clinical setting, it is a goal to maximize the data obtainable from relatively small test sample volumes (microliters) during chemical blood analysis. Fabrication of a sensor sample chamber for holding a blood sample in contact with a sensor is desirable in this regard so that many determinations may be simultaneously performed on a test sample, for example, using a series of interconnected sensors, each constructed to detect a different analyte, from a small test sample volume. However, as a sample chamber is made smaller, the concentration of contaminants in a sample, as those released from sensor components themselves, especially components defining the sample chamber, and/or certain reaction products of the sensor itself is increased. Such contamination may result in premature sensor failure.

Lactate electrode sensors include an enzyme-containing layer which converts lactate to reaction products including hydrogen peroxide according to the following reactions:

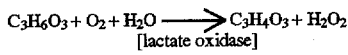

In these reactions, lactate reacts with oxygen to form hydrogen peroxide. A suitable electrode can then measure the formation of hydrogen peroxide, as an electrical signal. Current is generated as a result of peroxide oxidation, and under suitable conditions the current is proportional to the lactate concentration.

Numerous devices for determination of lactate have been described, however most of them have some limitation with respect to reproducibility, speed of response, test same volume, number of effective uses, and the range of detection. Some existing commercial methods rely on utilization of hydrogen peroxide measurement as outlined above.

Some known enzyme electrodes have a two membrane system. In these electrodes, the blood, including lactate and certain interferants, diffuses through a primary membrane of the sensor. Certain blood components then reach a second membrane and interact with an enzyme, such as lactate oxidase, that catalyzes the conversion of lactate to hydrogen peroxide. The hydrogen peroxide may diffuse back through the primary membrane, or it may further diffuse through the second membrane to an electrode where it can be reacted to form oxygen and a proton, resulting in a current proportional to the lactate concentration.

The electrode's membrane assembly serves several functions, including selectively allowing the passage of lactate therethrough, providing a location between the primary and secondary membranes for an enzyme to catalyze the reaction of lactate and oxygen passing through the primary membrane, and allowing only hydrogen peroxide through the secondary membrane to the electrode.

A single-layered electrode membrane was described by Jones in EP Patent No. 207 370 B1. This reference is directed to an electrochemical sensor including three primary components: a metal electrode, a reactive layer of immobilized enzyme directly on an anode, and a single-layered membrane. The membrane is formed from a dispersion of a polymerizable silicon-containing compound applied in an incompletely cured form, having a liquid carrier which is essentially insoluble in the dispersed phase and removable from the dispersion during curing.

It has been found, however, that the single membrane layer disclosed in EP 207,370 B1 minimizes only anionic interfering substances, such as ascorbic acid and uric acid, from passing therethrough. Neutral species, such as acetaminophen, can diffuse through the membrane and influence the sensor's sensitivity and accuracy.

As noted above, enzyme electrodes convert lactate or glucose into hydrogen peroxide, which can be reacted to produce a current proportional to the lactate or glucose concentration. Enzyme electrodes adapted to measure other analytes have also been described in the art. An enzyme electrode having an electrically conductive support member which consists of, or comprises, a porous layer of resin-bonded carbon or graphite particles is disclosed by Bennetto et al., in U.S. Pat. No. 4,970,145. The carbon or graphite particles have a finely divided platinum group metal intimately mixed therewith, to form a porous, substantially homogeneous, substrate layer into which the enzyme is adsorbed or immobilized. The preferred substrate materials are resin bonded, platinized carbon paper electrodes, comprising platinized carbon powder particles bonded onto a carbon paper substrate using a synthetic resin, preferably polytetrafluoroethylene, as the binder. These electrode materials are manufactured by depositing colloidal size particles of platinum, palladium, or other platinum group metal, onto finely divided particles of carbon or graphite, blending the platinized or palladized carbon or graphite particles with a fluorocarbon resin, preferably polytetrafluoroethylene, and applying the mixture onto an electrically conductive support, such as carbon paper, or a filamentous carbon fiber web.

The above-referenced enzyme electrodes require premolding of the graphite or carbon base often under conditions requiring sintering of the molded compact to fuse the binder, which, as noted, is a high melting point hydrophobic synthetic resin. These high temperatures could destroy enzymes, such as lactate oxidase.

Enzyme electrodes comprising an enzyme or mixture of enzymes immobilized or adsorbed onto a porous layer of resin bonded platinized or palladized carbon or graphite particles without a high temperature binder have been disclosed by Mullen, in U.S. Pat. No. 5,160,418. Mullen disclosed that the high temperature binders can either be dispensed with entirely or replaced by a low temperature, preferably water soluble or water dispersible binder, such as gelatin (a binder which can be activated at room temperature, which does not require high temperature sintering).

An aqueous solution of known analyte concentration is usually used to calibrate enzyme electrodes by measuring the current output for a fixed known lactate concentration. Over time, the current output for a fixed lactate concentration may change due to changes in enzyme activity, active enzyme content, membrane permeability or other factors. Therefore, by measuring the current associated with an unknown lactate concentration in a solution, the lactate concentration can be more accurately calculated based on the current generated from the known lactate concentration in the calibrator. There is often an inherent difference in the response for the analyte between the enzyme electrode in the aqueous calibration solution and the enzyme electrode in the unknown solution. However, to ensure reliable calibration, this difference in response between the enzyme electrodes of the two solutions, commonly referred to as the blood/aqueous slope ratio, should not change over time.

Despite the above improvements in the art, however, a need remains for accurate, multi-use lactate sensors, incorporating an improved lactate and oxygen-permeable membrane and an enzyme electrode, which sensors can provide a relatively stable blood/aqueous slope ratio. In addition, there is a need for an electrochemical sensor package which can be used with a small blood sample and for extended sampling or uses in a clinical setting. An electrochemical sensor of this type that does not require maintenance, i.e. remembraning, electrode cleaning, etc. would also be desired.

SUMMARY OF THE INVENTION

Therefore, it is an object of the present invention to provide a sensor having an improved membrane for sensing analytes in biological fluids.

It is another object of the present invention to provide such a sensor that can be used to accurately and conveniently determine lactate concentration in a biological fluid.

It is yet another object of the present invention to provide a method of making such a sensor.

It is still a further object of the present invention to provide such an electrode sensor that is capable of accurately and conveniently determining lactate concentrations in biological fluids.

It is yet a further object of the present invention to provide a method of making such an electrode sensor.

In one illustrative embodiment, the present invention provides a sensor for measuring a concentration of an analyte in a solution. The sensor comprises a substrate layer, an electrode layer, an immobilized enzyme layer and a hydrophobic layer. The substrate layer is formed from an electrically insulating material. The electrode layer is formed from an electrically conductive material, and the electrode layer is supported by the substrate layer. The immobilized enzyme layer is supported by the electrode layer, and the hydrophobic layer is supported by the immobilized enzyme layer. The immobilized enzyme layer has a hydrophobicity, and the hydrophobic layer has a hydrophobicity which is greater than the hydrophobicity of the immobilized enzyme layer. The sensor can be completed for use by addition of an enzyme containing layer in the form of an enzyme disposed within a polymer matrix, which layer is disposed along the hydrophobic layer at a location above the immobilized enzyme layer. An outer membrane layer is then applied.

In another illustrative embodiment, the present invention provides a method of making a sensor for measuring a concentration of an analyte in a solution. The method comprises the steps of: providing a substrate layer; disposing an electrically conductive layer along a surface of the substrate layer to form an electrode layer; disposing a layer including an enzyme immobilized to a support material along a surface of the electrode layer to form an immobilized enzyme layer; and disposing a hydrophobic layer along a surface of the immobilized enzyme layer.

In a further illustrative embodiment, the present invention provides a sensor for measuring a concentration of an analyte in a solution. The sensor is formed from a substrate layer, an electrode layer and an immobilized enzyme layer. The immobilized enzyme layer has a hydrophobicity. The electrode layer is disposed on the substrate layer, and the immobilized enzyme layer is disposed on the electrode layer. The improvement of this embodiment comprises a hydrophobic layer which has a hydrophobicity greater than the hydrophobicity of the immobilized enzyme layer. The hydrophobic layer is supported by the immobilized enzyme layer.

In yet a further illustrative embodiment, the present invention provides a sensor for measuring a concentration of an analyte in a solution. The sensor comprises a substrate layer, an electrode layer, an immobilized enzyme layer and an enzyme-polymer layer. The substrate layer is formed from an electrically insulating material. The electrode layer is formed from an electrically conductive material, and the electrode layer is supported by the substrate layer. The immobilized enzyme layer includes an enzyme immobilized in a support member, and the immobilized enzyme layer is supported by the electrode layer. The enzyme-polymer layer includes an enzyme, and the enzyme-polymer layer is disposed above the immobilized enzyme layer.

In still a further illustrative embodiment, the present invention provides a sensor for measuring a concentration of an analyte in a solution. The sensor is formed from a substrate layer, a dielectric layer, an electrode layer and an immobilized enzyme layer. The electrode layer is disposed on the substrate layer, the dielectric layer is disposed on the substrate layer, and the immobilized enzyme layer is disposed on the electrode layer. The improvement of this illustrative embodiment comprises an enzyme-polymer layer which includes an enzyme. The enzyme-polymer layer is disposed above the immobilized enzyme layer.

It is a feature of the present invention to provide an improved sensor which includes a layer having an enzyme disposed within a polymer matrix. This layer can delay the onset of nonlinear behavior by the sensor by providing an increased amount of enzyme within the sensor, reducing the diffusion of enzyme out of the sensor and/or increasing the distance between the analyte solution and the immobilized layer of enzyme.

It is another feature of the present invention to provide a sensor which includes a hydrophobic layer which is displaced between an immobilized enzyme layer and an enzyme/polymer layer such that the enzyme/polymer layer is restricted to an area above the immobilized enzyme layer.

BRIEF DESCRIPTION OF THE DRAWINGS

The above and other features, objects and advantages of the present invention will be better understood from the following specification when read in conjunction with the accompanying drawings, in which:

FIG. 5 is a magnified partial view of a sample chamber of the sensor package shown in FIG. 2;

FIG. 6 is a cross-sectional side view of the sample chamber shown in FIG. 5, taken along section line 6—6;

FIG. 7 is a cross-sectional side view of the sample chamber shown in FIG. 6, taken along section line 7—7;

FIG. 8 is a cross-sectional side view of the sample chamber shown in FIG. 5, taken along section line 8—8;

DETAILED DESCRIPTION OF THE INVENTION

Figure 1:
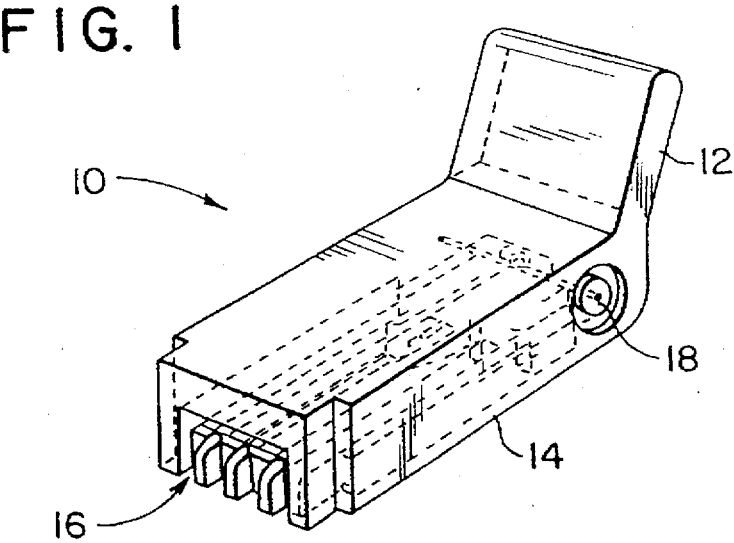
FIG. 1 is a perspective view of an electrochemical sensor package of the prior art.

Referring now to the drawings, in which like reference numerals designate like or corresponding parts throughout the several views, an assembled electrochemical sensor package in accordance with the prior art is illustrated in FIG. 1. Package 10 has a generally J-shaped body, including a handle portion 12, a main body 14, contact portion 16, and fluid or liquid passageway 18.

Figure 2:
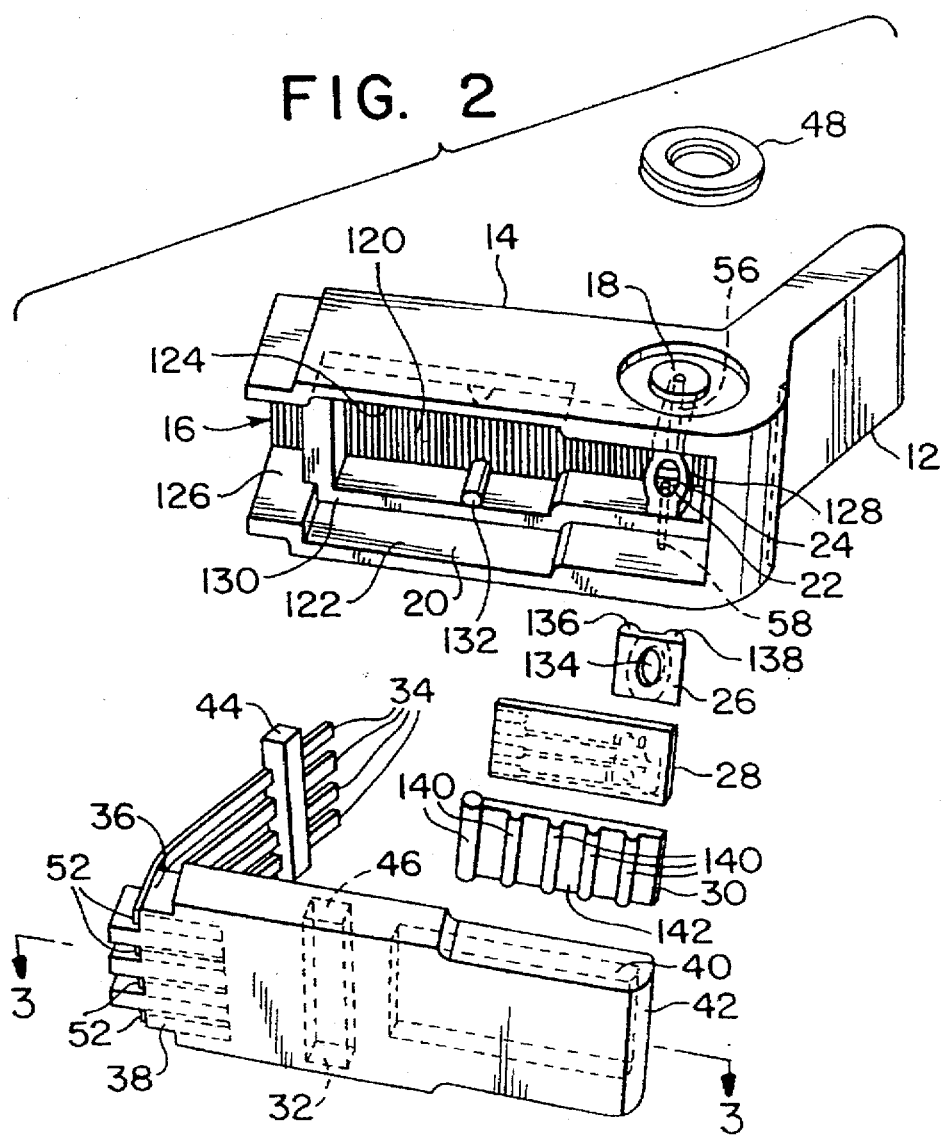
FIG. 2 is an exploded view of the components of the sensor package shown in FIG. 1.

The internal components of sensor package 10 are shown in an exploded view in FIG. 2. Package 10 includes a J-shaped housing 20 having a recess 22 formed therein. The recess 22 which forms a part of a sample chamber 54 (FIG. 5) includes an outer perimeter 24 and at least one passageway 18. Housing 20 has a substantially flat upper portion 120, sidewalls 122, 124, a frontal opening 126, and a rear wall 128 which is contiguous with sensor package handle portion 12. Housing 20 further includes a depressed inner rim 130 and projections 132 which contact the lead frame 32 when package 10 is assembled. A gasket 26 is provided to contact, and form a seal between, the housing perimeter 24 and a sensor 28. Gasket 26 is substantially rectangular-shaped and includes a substantially oval-shaped opening 134, and two raised surfaces 136, 138 which run along the length of gasket opening 134. Gasket raised portions 136, 138 allow gasket 26 to fit around the housing recess perimeter 24, while also allowing recess 22 to be exposed to sensor 28. A sensor pad 30 is provided to support sensor 28. Sensor pad 30 includes a series of transverse protrusions 140 on rear side 142 which provide sensor 28 with added support when package 10 is assembled. Lastly, a contact lead frame 32 is provided to electrically connect sensor 28 to an instrument (not shown) which can measure and convert a current to determine analyte concentration (e.g., lactate). Contact lead frame 32 includes four leads 34 secured to a base 36 at a first end portion 38, and a sensor recess 40 at a second end portion 42. The lead frame 32 can also include a stabilizer bar 44 for holding the leads in a predetermined position with respect to each other and aligning the leads 34 with the sensor 28. An additional recess 46 can be included for receipt of stabilizer bar 44. It is also noted that an electrode O-ring 48, commercially available from Ciba Corning Diagnostics Corp. or the like, can be provided to maintain a seal between adjacent sensor packages, or a fluid conduit (not shown), each different sensor used to simultaneously detect different analytes from the same fluid sample.

Figure 3:
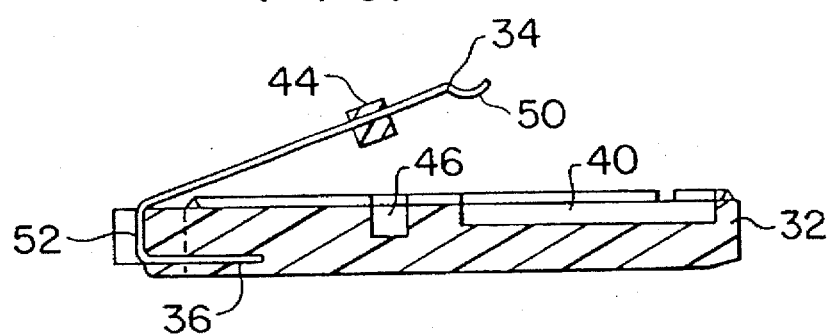
FIG. 3 is a cross-sectional side view of a contact lead frame shown in FIG. 2, with its leads partially open, taken along section line 3—3.
Figure 4:
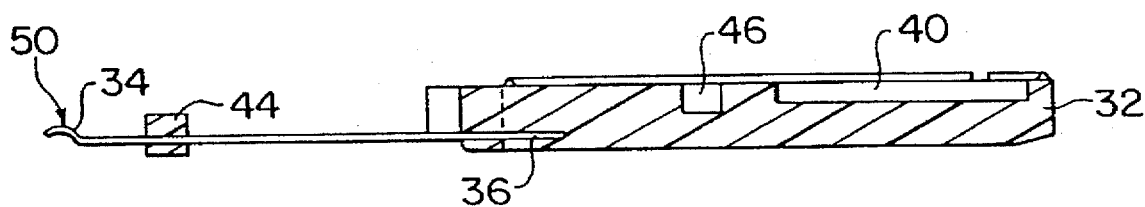
FIG. 4 is a cross-sectional side view of the contact lead frame shown in FIG. 3, with its leads wide open.

Referring now to FIGS. 3 and 4, a cross-sectional side view of contact lead frame 32 taken along section line 3—3, is shown with its leads partially and wide open. As noted above, to provide an interface system between an instrument and contacts on the sensor 28 (described below), contact lead frame 32, including plural leads 34 secured to base 36 at end portion 38, is provided. Leads 34 are typically made from a highly conductive, malleable metal, such as copper. Preferably, leads 34 are made of a highly conductive, malleable material, which is beryllium, silver, gold, or platinum plated, due to the lower cost of plated material. Most preferably, photo-etched, gold plated leads 34 are used due to their high conductivity. The leads 34 are molded into one end 38 of the contact lead frame 32. Lead frame 32 can be formed of any material that is compatible with, and can be secured to, the sensor package housing 20. Typically, lead frame 32 is made from a rigid, durable material such as glass, ceramic, stainless steel, or a plastic material such as acrylic, polyester, polycarbonate, polyvinyl chloride, and the like. Preferably, an acrylic plastic material, such as V825 acrylic, available from Rohm & Haas Corp., Philadelphia, Pa., is used to mold lead frame 32 due to its strength, durability, relatively low cost and ease of processing.

During assembly of the sensor package 10, sensor 28 is placed into recess 40 and leads 34 are bent around the lead frame 32 until they make contact with the sensor. Leads 34 contact the sensor with rounded spring tips 50 which apply constant pressure on the sensor contacts. Stabilizer bar 44, which aligns the leads 34 with the sensor contacts, is secured in recess 46 after the leads are bent around the frame.

Preferably, the stabilizer bar, if present, is solvent cemented in place in recess 46. Instrument contact surfaces 52, which are exposed after the sensor package 10 is assembled, are formed as the leads are bent over the frame (as shown in FIG. 3). Once the leads are in contact with the sensor, housing 20 is placed over the lead frame 32. The housing and lead frame are then secured together by being snap-fit, ultrasonically welded, adhesive bonded, or by other methods known to those skilled in the art.

Referring now to FIGS. 5–8, a magnified view of a sample chamber 54 of the sensor package 10 is shown. As noted above, sample chamber 54 is defined by the housing 20, the outer perimeter 24 around recess 22, gasket 26, and the sensor 28. At least one passageway 18, having an inlet 56 and an outlet 58, is provided to allow passage of a fluid sample, such as blood, into and out of sample chamber 54. Although, in the embodiment illustrated, inlet 56 and outlet 58 pass through housing 20, these openings can be formed in any manner to provide a passageway through which a fluid sample could reach sample chamber 54. For example, openings, or channels, could be formed in the gasket 26, or other part(s) of the sensor package 10.

The sample chamber 54 of the present sensor package 10 also includes a velocity compensator 60 (Bump), which reduces the internal volume of the chamber and creates a cross-sectional area close to that of the inlet 56 and outlet 58. The cross-sectional area of the sample chamber at the velocity compensator approaches that of the inlet and outlet. The velocity compensator or bump acts as a structural director of fluid flow.

Conventional sample delivery systems experience problems such as carryover of previous sample materials, and trapped air bubbles which are present or within the leading edge of the sample fluid to address a problem common to conventional sample delivery system. Typically, as a sample enters the chamber 54 its flow velocity abruptly slows until the chamber is full. The sample velocity then increases to its initial level, leaving the solution at the chamber walls stagnant. Although sample chambers are washed between measurements, air bubbles and fluid can become trapped in the chamber in stagnant areas. These air bubbles and residual fluid effect the accuracy of the sample measurement. The velocity compensator 60, therefore, keeps the flow velocity stable within the chamber, and reduces or eliminates the stagnant areas where bubbles and fluid can collect. The velocity of fluid flow through the sample chamber is substantially uniform in the presence of the velocity compensator. In addition, velocity compensator 60 allows the use of a large sensing area with relatively small inlet 56 and outlet 58 cross-sections. Because the cross-sectional area of the chamber 54 is reduced with the velocity compensator 60 in place, the ratio of sensing area to flow path is increased. This allows fluid samples to more efficiently contact sensor 28 as they are passed through package 10. Moreover, by positioning the velocity compensator 60 facing the sensor 28, samples are directed toward the sensor 28 while bubbles are substantially eliminated.

FIG. 6 illustrates a cross-sectional side view of the sample chamber 54, taken along section line 6—6. The velocity compensator 60 is shown as a molded part of housing 20. Although shown having a rounded shape, a variety of smooth, sloped shapes, without stagnant areas, can be used. Furthermore, although shown as a molded part of the housing, velocity compensator 60 can be a separate component, added to sample chamber 54.

Inlet 56 and outlet 58 portions are shown leading in and out of chamber 54. These sample paths typically have diameters between about 0.02 inch and about 0.04 inch; preferably, the diameters are about 0.03 inch. The sample chamber 54 has a sample diameter, with the velocity compensator 60, of at least the size of the sample paths to about 0.06 inch. FIG. 8 shows a side view of sensor package 10, taken along section line 8—8, through passageway 18. This view illustrates the relative sizes of the velocity compensator 60, sample chamber 54, and passageway 18.

Housing 20, as well as inlet 56 and outlet 58, and velocity compensator 60, can be fabricated from any material that is unreactive with a sample which passes into sample chamber 54 during analysis. For example, materials such as glass, ceramics, stainless steel, or plastic materials such as acrylic, polyester, polycarbonate, polyvinyl chloride, and the like.

Preferably, a clear, transparent acrylic plastic material, such as V825 acrylic from Rohm & Haas, is used to mold these parts due to its strength, durability, relatively low cost and ease of processing.

Gasket 26, shown in FIGS. 6 and 7, is typically formed from a material which, when held firmly between recess perimeter 24 and sensor 28, forms a seal around sample chamber 54 through which the passage of fluids is substantially prevented.

Typically, gasket 26 is formulated from a durable organic polymer which does not creep or flow when stressed, has a low durometer rating, and can be slightly hygroscopic. Preferably, a material used in the fabrication of gasket 26 has a hardness of between 10 and 100 on the Shore A scale; more preferably, a hardness of from about 40 to about 70 on the Shore A scale; and most preferably, a hardness of from about 45 to about 55 on the Shore A scale.

Because gasket 26 is typically an organic polymer, it is fabricated so as not to contain a substantial amount of any mobile extractable materials, such as plasticizers, which may leach into sensor 28. Additionally, as is the case for other sensor components as described above, it is important the material selected for formation of gasket 26 be free of any species which could migrate into a sample in chamber 54, affecting electrochemical measurements, and/or destroying sensor components. Material used in the formation of gasket 26 is preferably selected to be essentially free of mobile transition and main group metals, especially battery metals such as iron, cobalt, nickel, lead, copper, extractables, and species such as sulfides which are deleterious to preferred electrode materials.

Gasket 26 is typically formed form a highly cross-linked elastomeric compound. Any elastomeric material which meets all the purity and physical requirements listed above may serve. Most preferably, Sarlink™ 2450 elastomeric material from DSM having a hardness of about 50 on the Shore A scale is used to form gasket 26.

Sensor pad 30, also shown in FIGS. 6 and 7, can be formed of a material similar to that used to form gasket 26. Pad 30 is formed of a durable organic polymer which does not creep or flow when stressed, and has a low durometer. Preferably, a material used to form pad 30 has a hardness of between 40 and 60 on the Shore A scale. Most preferably, a silicone rubber or material such as Sarlink 2450 is used to form pad 30.

A sample chamber 54 of any size can be fabricated. Fabrication of a large sample chamber may be advantageous in some circumstances. As noted above, however, in the field of electrochemical analysis of blood, it is commonly desirable to perform as many analyte analyses as possible on a very small volume of blood. Thus, it is desirable to fabricate sensor 28 with a sample chamber 54 that is as small as possible. A sensor may effectively be utilized for a period of at least thirty (30) days, or the measurement of at least one thousand (1,000) blood samples having a sample chamber with a volume of less than about 10.0 μl (microliters); and preferably, from about 3.0 to about 5.0 μl.

Figure 9:
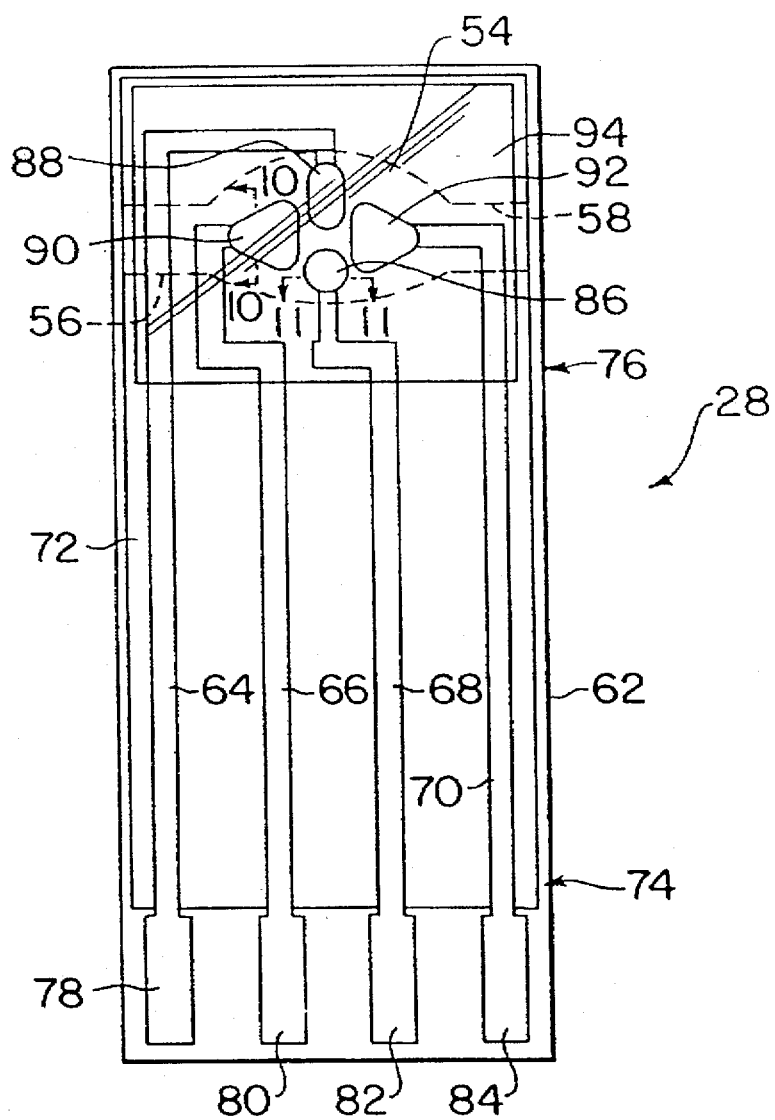
FIG. 9 is a magnified top plan view of a sensor used in the sensor package shown in FIG. 1.
Figure 10:
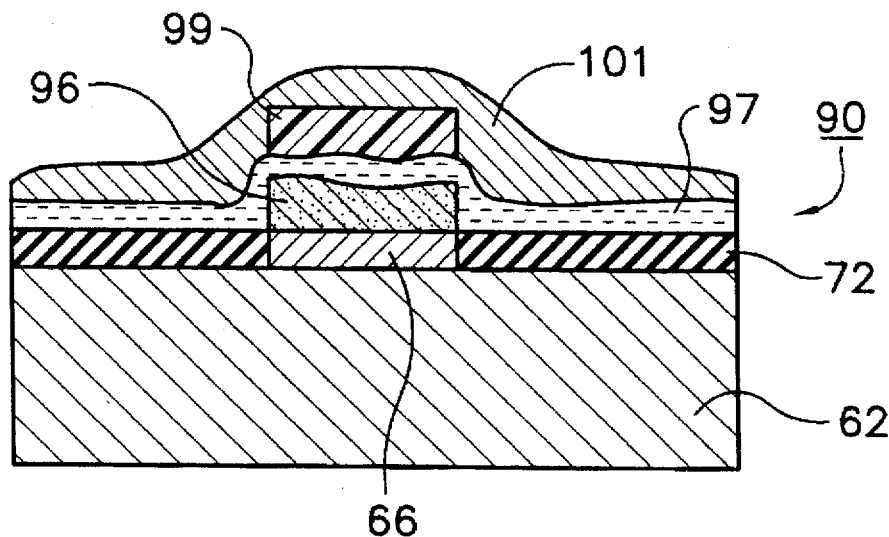
FIG. 10 is a cross-sectional side view of a working electrode according to the present invention.
Figure 11:
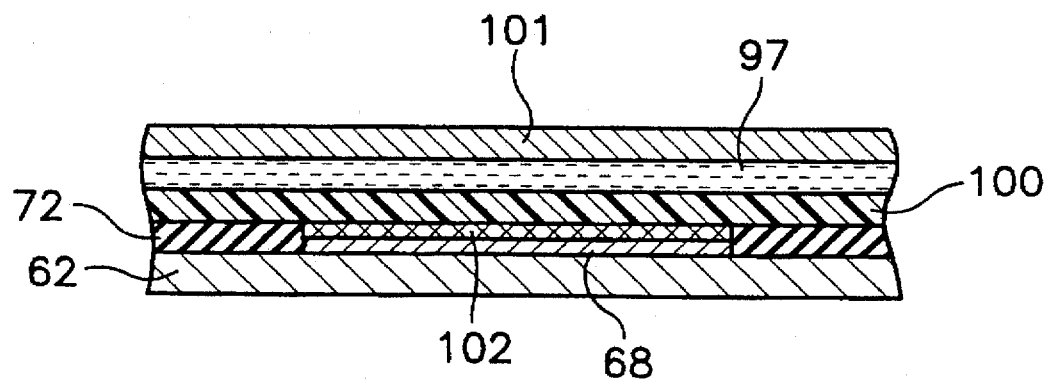
FIG. 11 is a cross-sectional side view of a reference electrode according to the present invention.

Referring now to FIGS. 9 through 11, a planar electrochemical sensor 28 is shown. FIG. 9 also shows phantom outlines of sample chamber 54, inlet 56 and outlet 58. These features are shown to illustrate the relative position of electrodes 86, 88, 90, and 92 described below to the flow path of a sample to be tested. Sensor 28 includes substantially planar substrate 62, conductive metal strips 64, 66, 68, and 70 deposited thereupon, and dielectric layer 72 deposited on substrate 62 so as to cover portions of conductive strips 64, 66, 68, and 70, while leaving portions of some of the strips uncovered.

Substrate 62 is formed from any substantially electrically insulating material such as ceramic, glass, refractory, polymers or combinations thereof. Formation of such an insulating substrate as a mechanical support or base is common knowledge to those of ordinary skill in the art. In the preferred embodiment, the substrate comprises approximately 96% alumina and approximately 4% glass binder. A suitable material comprising the preferred composition is available from Coors Ceramic Company, Grand Junction, Colo. Although a single substrate forms the foundation of sensor 28, a plurality of substrates can also be used, each supporting separate sensor components, and/or helping to support sensor components supported by other substrates.

Conductive strips 64, 66, 68 and 70 are deposited atop substrate 62 so as to extend from a first end 74 to a second end 76 thereof in a preferred embodiment. At first end 74, the conductive strips are typically deposited so as to be wide enough to define contact pads 78, 80, 82, and 84, respectively. At second end 76, the conductive strips are typically deposited so as to be somewhat narrower, exposed regions of which may define electrodes, as described below.

Conductive strips 64, 66, 68 and 70 may be deposited using well known thin or thick-film techniques. Typically, a compound including a metal is applied via typical thick-film screening to substrate 62, and the applied compound and substrate are then fired to sinter the active metal and to co-adhere the active metal to the substrate. The electroactive metal may comprise any conductive metal, for example, silver, platinum or gold, which is not oxidized or reduced in a potential range in which oxidation or reduction of any species to be measured occurs. Additionally, materials selected for fabrication of conductive strips 64, 66, 68 and 70 are desirably selected so as to be free of any impurities such as battery metals (electrochemically active in water) which are typically present in off-the-shelf materials commercially available for wire bonding, soldering, or welding. See EP-A-9481090.2 or U.S. Ser. No. 08/045,847 filed Apr. 9, 1993 which is incorporated herein by reference.

Many thick-film pastes suitable for use in the present invention are commercially available, such as a silver pastes available as product number 3571UF/Ag from Metech, Inc., of Elverson, Pa. (Metech), silver chloride available as product number 2539/Ag/AgCl from Metech; gold pastes available as product number PC10231/Au from Metech, and platinum paste available as product number PC10208/Pt from Metech.

With specific regard to conductive strip 66, which defines in part a working electrode 90 a preferred material is a very high purity platinum thick-film paste. Conductive strip 68 preferably comprises a layer of silver deposited atop substrate 62 with a layer of silver/silver chloride deposited thereupon in the electrode region, discussed below, to create a reference electrode 86. A layer of cellulose acetate is deposited atop the layer of silver chloride. Conductive strips 64, 66 and 70 comprise a platinum thick-film paste in preferred embodiments.

Employment of a silver reference electrode is within the scope of the present invention. Modification with respect to voltage settings, upon the substitution of a silver reference electrode for a silver/silver chloride reference electrode, would be easily made by one of ordinary skill in the art.

At the second end 76 of substrate 62, dielectric layer 72 is deposited so as to cover portions of conductive strips 64, 66, 68 and 70, while leaving portions of the conductive strips uncovered so as to define reference electrode 86, counter electrode 88, working electrode 90, interference correcting electrode 92, and contact pads 78, 80, 82, and 84. Material selected for fabrication of the dielectric layer 72 is desirably electrically insulating and non-porous, free of impurities which may be subject to oxidation or reduction in the potential range of any species or analyte to be measured, as described above, and is further selected so as to be free of mobile ions that would potentially carry charge and interfere with the activity of any electrolyte employed in the sensor. Further, dielectric 72 is selected so as to firmly adhere to substrate 62 and conductive strips 64, 66, 68, and 70, so as to allow electrodes 86, 88, 90, and 92 to be electrically addressable, while effectively electrically insulating portions covered by the dielectric. Materials such as ceramics, glass, refractory materials, polymeric materials, or combinations thereof are well known as dielectric materials and are suitable for use as a dielectric in the present invention. A preferred material is commercially available as Product Number 9615, a ceramic material from E. I. DuPont de Nemours & Co., Electronics Department, Wilmington, Del.

With respect to materials advantageously selected for fabrication of conductive strips 64, 66, 68, and 70, it is noted that material selection becomes less important in regions of the strips which define contact pads 78, 80, 82 and 84 and which connect the bonding pads to regions which define electrodes. For example, the contact pads and regions of the conductive strips connecting them to the electrodes may be fabricated from any conducting material that adheres to substrate 62 and that does not interfere with the electrical insulation function of dielectric layer 72. According to one embodiment, the contact pads and regions of the conductive strips connecting them to the electrodes are fabricated from a gold paste.

In addition to the material selection parameters discussed above, and as discussed with respect to selection of the dielectric material, it is advantageous in the fabrication of a sensor to select materials for fabrication of the substrate, the conductive strips, and the dielectric layer such that good adherence is achieved between adjacent layers, that is, delamination is minimized as explained in EP-A-94810190.2. If good adherence is not achieved, reference, counter, working and interference correcting electrodes 86, 88, 90, and 92, will not be well-defined which in one embodiment is defined by a screen used in the thick-film deposition process, and disadvantageous electrochemistry will result.

A cross-sectional side view of working electrode 90 is illustrated in FIG. 10. As described above, conductive strip 66 is deposited upon substrate 62, and dielectric layer 72 covers portions of conductive strip 66 leaving a portion uncovered to define a working electrode area. An active layer 96 is deposited upon conductive strip 66 using techniques similar to the deposition of conductive strips 64, 66, 68 and 70. Hydrophobic layer 97, enzyme/polymer layer 99 and membrane layer 101 are consecutively placed above active layer 96.

Preferably, layer 96 has a thickness of about 10 micrometers to about 30 micrometers, more preferably from about 15 micrometers to about 25 micrometers and most preferably about 20 micrometers. When observed in a direction perpendicular to the cross-section of FIG. 10 (i.e., a top view of sensor 90), layer 96 preferably has an area of from about 0.13 square micrometers to about 0.28 square micrometers, more preferably from about 0.16 square micrometers to about 0.24 square micrometers and most preferably from about 0.19 square micrometers to about 0.20 square micrometers.

Typically, thick-film screen printing at low temperature is used to apply an active layer 96 in the form of a paste to conductive strip 66 in order to limit thermal damage to the enzyme. Active layer 96 comprises a catalytically active quantity of a catalyst immobilized onto an electrically conducting support member which consists of or comprises a porous layer of resin-bonded carbon or graphite particles. Such a catalyst is typically an enzyme. Preferably, the catalyst is lactate oxidase. The particles have intimately mixed therewith, or deposited or adsorbed onto the surface of the individual particles prior to bonding to form the layer, a finely divided platinum group metal to form a porous, substrate layer onto which the enzyme is adsorbed or immobilized and comprising a substantially heterogeneous layer of resin-bonded carbon or graphite particles with the platinum group metal adsorbed on the carbon or graphite particles. An enzyme immobilized or adsorbed onto a porous layer of resin bonded platinized carbon particles is disclosed by Mullen, in U.S. Pat. No. 5,160,418 and Bennetto et al., in U.S. Pat. No. 4,970,145, both of which are incorporated by reference. The active layer 96 may alternatively be formed by first depositing the finely divided platinum group metal, optionally preadsorbed onto or admixed with finely divided carbon or graphite, with or without all or some of the resin binder, if used, on the surface of the electrically conductive substrate, or conductive strip 66.

The platinum group metal in finely divided elemental form, including platinum, palladium, iridium, or rhodium, may be replaced by the corresponding oxides, such as platinum or palladium oxide. Therefore, all references herein to a platinized material are to be taken as including a platinum group metal, as described above, and/or corresponding oxides-containing material unless the context requires otherwise.

Any suitable carbon or graphite powder which readily permits the subsequent immobilization of an enzyme may be used to form the active layer. To this end, carbon powder should be used having a high density of functional groups, such as carboxylate, amino and sulfur-containing groups, on the surface, as opposed to the more vitreous and glassy carbons, which bind enzymes only poorly. Typically, carbon or graphite powder particle size ranges from between about 3.0 and about 50.0 nm; preferably, particle sizes range from between about 5.0 and 30.0 nm.

Platinum may be deposited on the carbon particles in any convenient fashion, for example, vapor phase deposition, electrochemical deposition, or simple adsorption from colloidal suspension to give platinum group metal loadings in the range of between about 0.1 to about 20.0 percent, by weight, based on the weight of carbon. Preferably, the platinum group metal loadings are between about 5.0 to about 15.0 percent by weight. These limits are, however, practical rather than critical. Below about 1.0 percent platinum group metal, the output signal falls to a level which, in practical terms, is too low to be measured except by very sensitive apparatus; above about 20.0 percent, the loading of platinum group metal becomes uneconomic, with little additional benefit in terms of increased response or sensitivity. In the preferred technique, the carbon powder is platinized by the oxidative decomposition of a platinum compound such as chloroplatinic acid or, more preferably, a complex of platinum or palladium with an oxidizable ligand, in the presence of the carbon powder, thereby to deposit colloidal size platinum or palladium direct upon the surface of the carbon particle, in the manner taught, for example, by Petrow et at., in U.S. Pat. Nos. 4,044,193 and 4,166,143, both of which are incorporated herein by reference. Preferably, the platinum group metal or oxide particles have a particle size in the range of between about 1.0 nm to about 20.0 nm, and most preferably are of a colloidal size in the range of between about 1.0 nm to about 4.0 nm.

The preferred active layer substrate used in accordance with the present invention are, in fact, commercially available materials, sold under the name PLATINUM ON CARBON BLACK from E-TEK, Inc., Framingham, Mass. An enzyme, such as glucose oxidase, or lactate oxidase, can be immobilized with platinized carbon powder particles, prepared by the deposition of colloidal platinum having a particle size of between about 1.5 to about 2.5 nm onto the carbon powder, having a nominal particle size of about 30.0 nm, by the oxidative decomposition of complex platinum sulfite acid (II) using $H_2O_2$.

In the present invention, the platinum activated carbon is treated in a phosphate buffer formulation having a pH of about 7.5. The platinum activated carbon is added to the buffer to neutralize any sulfuric acid present from the formation of the platinized carbon powder particles. To the platinum activated carbon and buffer mixture a co-protein, such as bovine serum albumin, is added to adsorb onto the carbon. The bovine serum albumin is added to help stabilize the enzyme, such as lactate oxidase, as is known to those skilled in the art. A hydrophobic binder, such as a polyester formed from a diacid and a diol is then added in solution form to the bovine serum albumin-platinum activated carbon mixture. Generally, the binder should be capable of acting as a theology modifier that allows printing of the mixture and adhesion of the mixture after the solvent evaporates. One example of such a hydrophobic binder is the commercially available resin solution sold under product number 8101RS from Metech. Typically, such resins are the reaction product of a phthalic acid, such as teraphthalic acid or isophthalic acid, and a diol, such as ethylene glycol. While particular formulations of the hydrophobic binder have been disclosed herein, it is to be understood that other hydrophobic binders are contemplated to be appropriate for use in the present invention. Such hydrophobic binders should be capable of holding the components of the active layer together after evaporation of the solvent. Preferably, these hydrophobic binders should also be able to serve as rheology modifiers that allow printing of the mixture with tighter resolution.

To this mixture, a surfactant may be added to provide better printing flow characteristics when active layer 96 is screen printed upon conductive strip 66. An additional benefit of the surfactant is to act as a wetting agent for the sensor during use. The active layer 96 being comprised of a hydrophobic binder becomes difficult to wet with water after it is fully dried. The surfactant facilitates this hydration. The surfactant material used can be any liquid surfactant, known to those skilled in the art, which is water soluble and exhibits a hydrophilic lipophilic balance (HLB) in the range of 12–16. Typical surfactant materials for use in this regard can be alkylarylpolyether alcohols, such as alkylphenoxypolyethoxyethanol. One such material is sold under the trademark Triton® from Union Carbide Chemicals and Plastics Co., Inc., Danbury, Conn. The preferred material for use in the present application is Triton® X-100 surfactant (HLB 13.5). After these components are milled, a resin thinner may be added to adjust the active layer 96 viscosity for printing purposes. Typically, a petroleum solvent-based resin thinner is used to bring the paste viscosity within the range of between 10,000 to about 100,000 centipoise. Resin thinners for this purpose are commercially available as product number 8101 thinner from Metech. An enzyme, such as lactate oxidase, is then added to the mixture, and the final paste is screen printed upon conductive strip 66. Other enzymes may be similarly added to the mixture to prepare active layers specific for other analytes.

Hydrophobic layer 97 is formed from at least one material having a greater hydrophobicity than active layer 96 so that layer 99 beads on layer 97 thus reducing or eliminating hydrophilic materials placed on layer 97 from spreading to other areas of electrode 90 (e.g., dielectric layer 72). "Hydrophobicity" herein denotes the lack of affinity for water. The hydrophobicity of a material can be measured by sessile drop contact angle measurements, in which a first layer of material is more hydrophobic than a second layer of material if the first layer of material has a water droplet advancing angle which is greater than the water droplet advancing angle of the second layer of material. Methods of performing sessile drop contact angle measurements are known to those skilled in the art and can be carried out on, for example, any commercially available goniometer. Preferably, layer 97 has a water droplet advancing angle of from about 60° to about 100°, more preferably from about 75° to about 100° and most preferably from about 90° to about 100°. Active layer 96 preferably has a water droplet advancing angle of from about 0° to about 20°.

It is to be noted that it is not necessary that layer 97 promote adhesion between active layer 96 and any other layers. In certain embodiments, however, hydrophobic layer 97 may promote adhesion between active layer 96 and enzyme/polymer layer 99. Typically, layer 97 is a silane, although other materials may be used so long as they act as a hydrophobic layer while providing the improved properties of the present invention as described herein. Silanes appropriate for use in layer 97 include, but are not limited to aminosilanes, aminoalkylalkoxysilanes, chlorosilanes, alkylsilanes and alkylalkoxysilanes. Preferably, layer 97 is formed from aminopropyltriethoxysilane.

Layer 97 may be applied by a variety of techniques as known to those skilled in the art including spin coating, spraying and dipping. Because layer 97 is applied onto active layer 96, it is preferable that layer 97 be applied using a process that is not harmful to the immobilized enzyme disposed within layer 96. Accordingly, in a preferred embodiment, layer 97 is formed by pouring an aqueous solution of one of the aforementioned materials on top of layers 96 and 72 (FIG. 10), letting the solution sit for a period of time, draining the solution, and removing excess solution by spinning with a spin coating apparatus. The surface is then cured at room temperature for 24 hours. In a particularly preferred embodiment, this technique is used with a 5% by weight aqueous solution of aminopropyltriethoxysilane with the step of drying being performed for a time period of 24 hours at a relative humidity of less than about 60%. It is to be noted that it has been found to be advantageous to minimize the amount of time between preparation of the solution and application of the solution. Preferably, this time period is at most about 30 minutes.

For most applications, layer 97 need only be comprised of approximately one monolayer. Accordingly, in certain embodiments, it is preferable that layer 97 have a thickness of about 0.1 micrometer. However, while a particular thickness for layer 97 has been disclosed herein, it is to be understood that layer 97 is not limited by thickness. Layer 97 may have any thickness so long as layer 97 acts as a hydrophobic barrier to active layer 96 while allowing active electrode 90 to provide the advantageous properties of the present invention as described herein.

Enzyme/polymer layer 99 is designed to increase the time period over which the blood/aqueous slope of enzyme electrode 90 is linear. To assist in achieving this goal, layer 99 should only be disposed in an area above the area defined by active layer 96 (i.e., layer 99 should only be disposed above the analyte sensing portion of electrode 90 formed by active layer 96). In particular, it is to be noted that layer 99 should not extend above the area corresponding to inactive electrode 92 because, if layer 99 does extend above electrode 92, electrode 92 would also give a signal in the presence of an analyte, such as lactate. Thus, the area above electrode 92 should not be covered by layer 99 even though electrodes 90 and 92 may be spaced close to each other. Preferably, the area of layer 99 is from about 40% to about 100% the area of layer 96, more preferably from about 50% to about 95%, and most preferably from about 60% to about 90%. Confining the area of 99 is at least partially due to the difference in hydrophobicity between layer 97 and layer 99. Preferably, layer 99 has a thickness of from about 1 micrometer to about 30 micrometers, more preferably from about 5 micrometers to about 20 micrometers and most preferably from about 10 micrometers to about 15 micrometers.

In certain embodiments, layer 99 includes the same enzyme that is disposed within active layer 96. For these embodiments, if layer 96 includes lactate oxidase, layer 99 also includes lactate oxidase. Alternatively, for such embodiments, if layer 96 has glucose oxidase disposed therein, layer 99 should also comprise glucose oxidase.

In addition to the enzyme, layer 99 comprises a polymer that can act as a matrix in which the enzyme of layer 99 is stored which limits the diffusion of the enzyme from layer 99. To enhance the effects of layer 99, the polymer should have a comparatively low solubility in water under the use conditions of electrode 90 (i.e., about 37° C.). Preferably, the polymer has a relatively high solubility in water above room temperature and a relatively low solubility in water at room temperature so that enzyme/polymer layer 99 may be prepared as discussed below. Materials appropriate for use in layer 99 should also provide an environment which assists in maintaining the normal conformation of the enzyme. Thus, if the enzyme is lactate oxidase, the polymer should be capable of providing a hydrogen-bonding environment. An exemplary and nonlimiting list of polymers appropriate for use in enzyme/polymer layer 99 includes cross-linked polyvinyl pyrrolidone, cross-linked gelatine, polyhydroxyethylmethacrylate (PHEMA) and polyvinyl alcohol (PVOH).

In embodiments in which the enzyme in layer 99 is lactate oxidase, the polymer of layer 99 should be a polyhydric alcohol such as PVOH. Preferably, the polymer is 99.9% hydrolized PVOH (i.e., having less than about 0.1% acetate groups). It is to be noted that increasing the amount of hydrolysis makes the PVOH more difficult to dissolve in water at room temperature, but using a more soluble form of PVOH can cause the membrane to swell, ultimately causing the enzyme to wash out of the membrane. Preferably, the PVOH has a molecular weight from about 70,000 to about 300,000. PVOH having a higher molecular weight is more difficult to manipulate when preparing layer 99 as described below, and PVOH having a lower molecular weight can make the material too soluble.

Enzyme/polymer layer 99 may be prepared as follows. A slurry of the polymer and water is formed at room temperature then heated to dissolve the polymer. The solution is cooled to room temperature and the enzyme is added. The amount of polymer dissolved in the water varies depending upon the enzyme, polymer, the molecular weight of the polymer and analyte to be detected. For example, when lactate oxidase is used as the enzyme and 99.9% hydrolized PVOH having a molecular weight of from about 70,000 to about 300,000 is used as the polymer solution, the weight percent of PVOH dissolved in the water is preferably from about 2% to about 15%, more preferably from about 5% to about 10%, and most preferably about 7%. As the molecular weight of the PVOH is decreased, the water solubility of PVOH increases. Therefore, for higher molecular weight PVOH, these ranges decrease, and, for lower molecular weight PVOH, these ranges can increase. The amount of enzyme dissolved in the PVOH/water solution varies depending upon the enzyme, the PVOH and the analyte to be detected. When the enzyme is lactate oxidase and the polymer is 99.9% hydrolized PVOH having a molecular weight of from about 70,000 to about 300,000 is used, the weight percent of lactate oxidase dissolved in the PVOH/water solution is preferably from about 0.5% to about 10%, more preferably from about 3% to about 9% and most preferably about 4%. It should be noted that, while certain ranges of the relative amount of lactate oxidase present in enzyme/polymer layer 99 have been disclosed, it is to be noted that, under some circumstances, the amount of active enzyme within the lactate oxidase per unit mass may vary depending upon when the lactate oxidase was prepared and the amount of stabilizer added by the lactate oxidase vendor. Hence, under such circumstances, it may be advantageous to prepare enzyme/polymer layer 99 using the activity of the enzyme rather than the concentration of the enzyme to avoid problems with inconsistent shelf life of electrode 90.

Layer 99 may be applied to hydrophobic layer 97 using any technique known to those skilled in the art which is capable of limiting the location of layer 99 as discussed above. Since layer 96 is typically applied using a solvent process (e.g., screen printing), a loss in enzyme activity occurs during the application process. Thus, layer 99 is preferably applied using an aqueous process to increase the amount of available enzyme in electrode 90, resulting in a longer useful lifetime of electrode 90. In a particularly preferred embodiment, the above-noted solution used to form layer 99 is applied to layer 97 using a spotting work station comprising a syringe pump with fluid connections to a dispensing needle.

Figure 12:
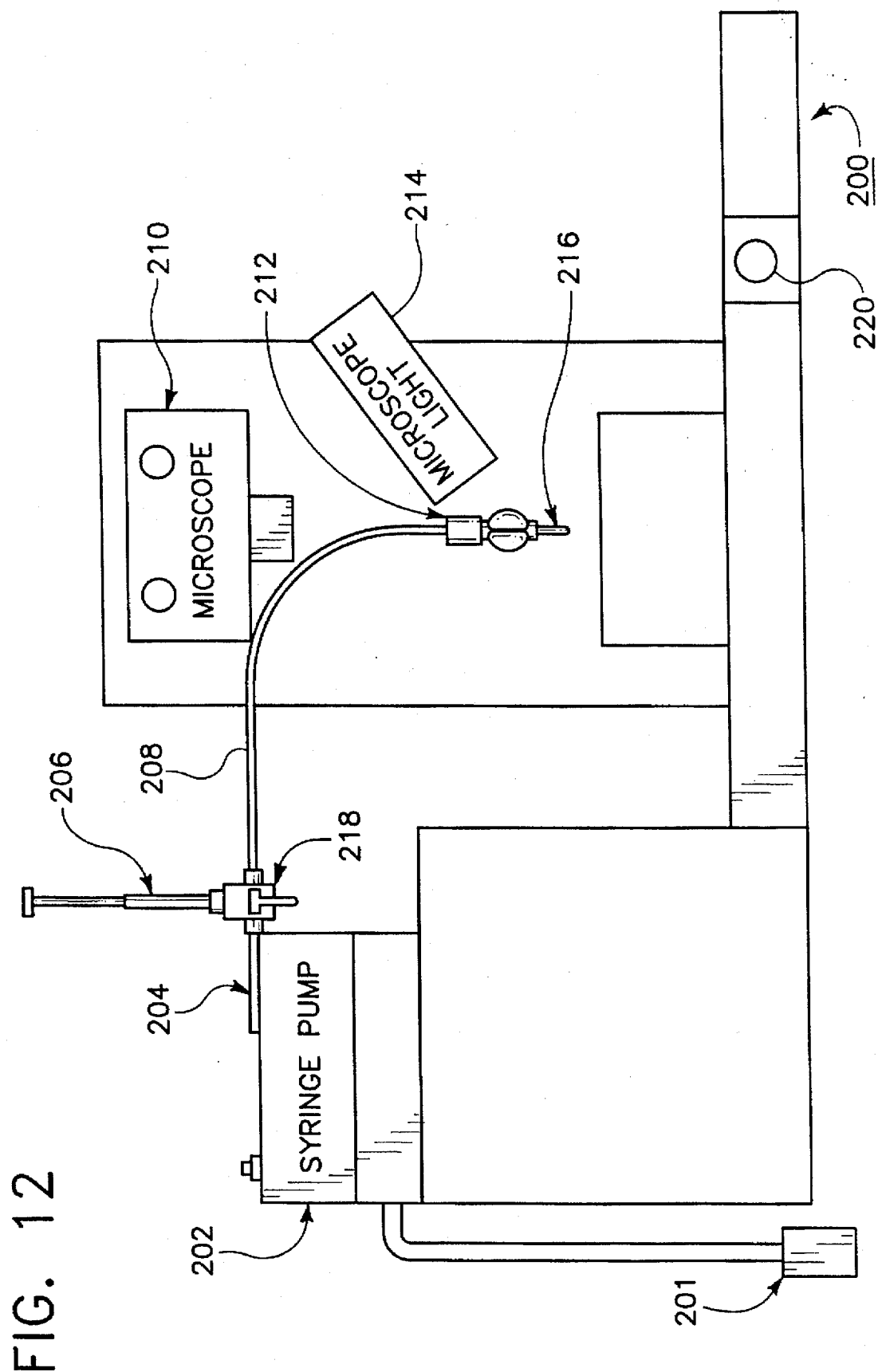
FIG. 12 is a schematic representation of a spotting workstation according to the present invention.

FIG. 12 depicts one embodiment of a workstation 200 appropriate for use in the present invention. Workstation 200 includes foot switch 201, syringe pump 202, dispensing syringe 204, filler syringe 206, tubing 208, microscope light 210, male fitting 212, microscope light 214, dispensing needle 216, three-way valve 218 and vertical positioner 220. The position of layer 97 relative to the dispensing needle 216 is verified using microscope 210. When layer 97 is located beneath needle 216, foot switch 201 is depressed by the user so that syringe pump 202 dispenses a small amount of solution used to form layer 30 through dispensing needle 216. Typically, workstation 200 is provided such that a 20 nanoliter (nL) aliquot of solution is dispensed by needle 216, although other quantities of solution may be dispensed so long as layer 99 provides the advantageous features described herein. Subsequent to being deposited on layer 97, layer 99 should be air dried at room temperature for about 2 hours to about 4 hours. Using this spotting technique to apply layer 99 has been observed to increase the useful lifetime of electrode 90 from about 2–3 days to about 7–15 days.

It is believed that the nonlinear blood/aqueous slope behavior of prior art electrode sensors may result from loss of activity or diffusion of enzyme from these sensors to the solution containing the analyte. According to the present invention, layer 99 increases the amount of enzyme present in electrode 90 which may assist in delaying the onset of such nonlinear behavior by electrode 90. In addition, the polymer of layer 99 may act to immobilize the enzyme, thereby reducing the rate of diffusion of the enzyme from electrode 90 to the analyte solution. Furthermore, layer 99 may reduce the rate of diffusion of the enzyme from electrode 90 to the analyte solution by increasing the distance between active layer 96 and the analyte solution.

Membrane layer 101 is formed from a polymeric material and a surfactant. In a preferred embodiment, layer 101 is a multilayer composite, with each individual layer being formed from the same polymeric material and surfactant. The polymeric material may be a polyurethane, silicone polymer or block copolymer. In certain embodiments, the polymeric material may be a filled composite structure, applied as a liquid emulsion. Polymeric materials appropriate for use in the present invention are disclosed in, for example, commonly assigned and co-pending U.S. patent application Ser. No. 08/508,273, now U.S. Pat. No. 5,582,698 which is herein incorporated by reference. The emulsion, which when dried, results in the polymeric material of layer 101 preferably has a viscosity of from about 20 Kcps to about 70 Kcps, more preferably from about 30 Kcps to about 60 Kcps and most preferably from about 35 Kcps to about 50 Kcps, as measured by the Brookfield technique using a Brookfield Rheometer with the small sample adaptor. According to the present invention, the polymeric material of membrane layer 101 is preferably the commercially available as FC-61 polymeric material from Dow Corning, Midland, Mich. This material is a low viscosity, filled, opaque emulsion. Typically, this material has a pH of about 11.0, and a viscosity of about 40 Kcps.

The surfactant used in layer 101 is provided to increase the slope of the sensor because a higher slope assists in the initial performance of electrode 90 by decreasing the initial bias drift relative to a reference value (i.e., decreasing the time for hydration). Surfactants appropriate for use in layer 101 should have both polar (i.e., hydrophilic) and nonpolar (i.e., hydrophobic) portions. Preferably, the surfactant is a nonionic surfactant. Examples of such materials include the Pluronic® family of surfactants, available from BASF located in Parsippany, N.J., and the Brij® family of surfactants available from ICI Specialty Chemicals located in Wilmington Del. The Pluronic® family of surfactants has the general formula:

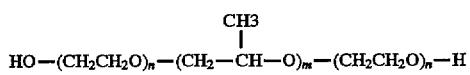

The Brij® family of surfactants, which include at least one hydrophobic chain bonded to an oligoalkylene oxide, has the general formula:

$CH_3-(CH_2)_n-O(CH_2CH_2O)_m-H$

Preferably the surfactant is Brij® 700 (n=17, m=100), Brij® 35 (n=11, m=25), Pluronic® F68 (n=80 m=27) or Pluronic® F108 (n=141 m=44).

The amount of surfactant in layer 101 should be such that electrode 90 has an acceptable day to day bias drift. If the amount of surfactant in layer 101 is too small, this desirable effect will not be achieved. However, it is believed that, if too much surfactant is incorporated into layer 101, the change in the slope of electrode 90 from day to day may be too large. Preferably, the weight percentage of surfactant within layer 101 is from about 0% to about 1%, more preferably from about 0.3% to about 0.8% and most preferably about 0.5%. In a particularly preferred embodiment, layer 101 comprises FC-61 polymeric material and about 0.5 weight percent Brij® 700. It should be noted that, when using FC-61 polymeric material as the polymeric material of layer 101, it has been observed that the bias drift of electrode 90 is unacceptable when certain phenoxy type surfactants are incorporated, such as Triton® X-100 or Makon® 10.

Each individual layer of membrane layer 101 is preferably formed from the same composition of polymeric material and surfactant. In a particularly preferred embodiment, layer 101 comprises four individual layers, each layer having the same composition of polymeric material and surfactant. Each layer is applied using a spin coating apparatus. The first layer (i.e., the layer applied directly to layer 99) is applied by completely flooding the surface of layer 99 with excess solution of the polymeric material and surfactant. The excess solution is then removed by spinning electrode 90 with a spin coating apparatus within about one minute of the start of application. The rest of the layers of which layer 101 is comprised are applied by spinning electrode 90 and dispensing the solution of polymeric material and surfactant directly onto the surface of the underlying layer. Preferably, layer 101 has a thickness from about 10 micrometers to about 100 micrometers and more preferably from about 20 micrometers.

Interference correcting electrode 92 (not shown) is formed in a manner similar to the working electrode 90. The interference correcting electrode 92, however, includes an inactive layer, rather than an active layer. The inactive layer of electrode 92 is made using the same components and method used in a process of forming the working electrode, but, instead of having an active enzyme, an inactive or nonreactive protein, such as bovine serum albumin is added to the mixture of bovine serum albumin-platinum activated carbon, resin, surfactant, and thinner. Moreover, interference correcting electrode 92 does not include a separate layer of enzyme dissolved in a polymer. Thus, for interference correcting electrode 92, the membrane layer, which comprises a polymeric material and a surfactant as discussed above, is disposed directly on the hydrophobic layer. As noted above, the interference correcting electrode serves to adjust for any interfering species, such as the neutral species acetaminophen, diffusing through the membrane layer on top of electrodes 86, 88, 90, and 92.

FIG. 11 shows a cross-sectional side view of reference electrode 86. Reference electrode 86, as noted above, is formed as a conductive strip 68, preferably comprising a layer of silver is deposited thereon. Dielectric layer 72 is deposited covering a portion of conductive strip 68, while leaving a portion uncovered to define the electrode areas and contact pads. In the embodiment depicted in FIG. 11, a silver/silver chloride layer 102 is deposited upon conductive strip 68 either by chloridizing with aqueous sodium hypochlorite (i.e., bleach) or by screen printing techniques known to those of skill in the art. Chloridizing with aqueous sodium hypochlorite can be achieved by exposing the silver to a 0.525% solution of NaOCl for about five minutes, followed by rinsing in distilled water and air drying. Silver/silver chloride reference electrode inks, such as those available as product number 2359 from Metech, are developed to provide a standard reference electrode utilizing the silver/silver chloride couple. To reduce problems with potential shifts caused by reference electrode 86, a cellulose acetate layer 100 can be disposed above layer 102. Layer 100 helps to shield reference electrode 86 from impurities due to its barrier properties to proteins and its ability to transport sufficient water and electrolytes to maintain a stable potential at the surface of the printed silver/silver chloride. Membrane layer 101, prepared as described above, is disposed along the surface of layer 100.

The choice of a proper solvent and cure process is critical in preparing a uniform cellulose acetate layer over the reference electrode. The solvent must have a low vapor pressure (high boiling point) in order to provide sufficient screen life for the printing process to be completed. It must be compatible with the printing screens, i.e. not degrade the screen emulsion during printing. The viscosity of the prepared paste must be relatively high, 40,000 centipoise to 350,000 centipoise. This mandates that the % solids of the polymer solution be fairly high, thus the solvent must be very good for the polymer. Suitable solvents include the so-called "super solvents", polar aprotic solvents such as dimethyl formamide, dimethylsulfoxide, hexamethylphosphoramide, and 1,3-dimethyl-2-imidazolidinone (DMI) are examples of this class of solvent, with DMI being the preferred solvent.

Solutions prepared in the concentration range of from 15 to 35 grams of cellulose acetate in 100 mL of DMI were found acceptable for the printing process. The preferred concentration was chosen as 20 grams cellulose acetate in 100 mL of DMI. In order to rapidly dissolve the polymer, the solvent is heated to between 60° and 100° C., with the preferred temperature being 95° C. The polymer is added to the rapidly stirred (magnetic stir bar), heated solvent (water bath with the temperature preset). It is then mechanically mixed in with a spatula, after which it is stirred continuously until completely dissolved. The polymer/solvent mixture (paste) is then removed from the water bath, allowed to cool to room temperature, labeled and set aside until needed for printing.

The paste is generally printed on the same day it is prepared, it can be used up to several months after preparation, however, performance of the layer gradually decreased with paste shelf life. The paste is applied in a 2 pass print after which it is allowed to level for a period of time no less than 10 minutes and no more than one hour. It is cured in a box oven at 55° C. for 10 minutes, the temperature of the oven is then ramped up to 100° C. over a 10 minute period, the curing continues for 10 minutes more at this temperature. This print method/cure cycle is crucial to the performance of the cellulose acetate membrane. Low cure temperatures do not remove sufficient solvent, while longer cures or higher cure temperatures lead to a brittle membrane which delaminates easily from the substrate, particularly after post-treatment of the sensor with an anti-drying agent. Printing with more passes leads to a thicker membrane, which is also prone to delamination. It is important not to completely remove solvent, as complete removal would hinder the hydration process.

Cellulose acetate layer 100 can be applied by a spotting technique or by a screen printing technique. If the spotting technique is used, an Asymtek XYZ table, available from Asymtek Corporation, Carlsbad, Calif., and known to those of skill in the art, can be used. Alternatively, spotting workstation 200 may be used. If a screen printing deposition process is used, a high viscosity solution from a high boiling solvent, such as listed above, can be used.

While noting that a variety of sensor configurations can be advantageous in different applications, the following non-limiting preferred dimensional specifications of a sensor 28 fabricated in accordance with a preferred embodiment of the present invention are given.

Substrate 62 can be fabricated in a variety of shapes and sizes. According to one specific preferred embodiment of the invention, substrate 62 is from about 0.4 inch to about 0.5 inch long; preferably, about 0.45 inch long. Substrate 62 is from about 0.15 inch to about 0.25 inch wide; preferably, about 0.18 inch wide. Substrate 62 is from about 0.02 inch to about 0.05 inch thick; preferably, about 0.025 inch thick. Conductive strips 64, 66, 68 and 70 are each deposited in a thickness of from about 10.0 microns to about 20.0 microns; preferably, the strips are about 15.0 microns thick. Conductive strips 64, 66, 68, and 70, at end 76 of the sensor, are from about 0.01 inch to about 0.03 inch wide, preferably about 0.01 wide. Contact pads 78, 80, 82, and 84 at end 74 of the sensor, are from about 0.025 inch to about 0.05 inch wide, preferably about 0.03 inch wide.

Portions of the conductive strips are exposed to define the reference electrode 86, counter electrode 88, working electrode 90, and interference correcting electrode 92. The exposed surface area for the reference electrode 86 is about 0.00015 inch$^2$, and for the counter electrode 88 is about 0.00022 inch$^2$. The working and interference correcting electrodes 90, 92, each have surface areas of about 0.00038 inch$^2$. These exposed surface area dimensional specifications do not take into consideration surface area due to the edges of the electrodes, defined by the thickness of the electrodes as deposited or the porosity of the layer. Such edge dimensions are minimal relative to the overall electrode areas. However, the exposed surface area specification are thus somewhat approximate.

According to an alternate embodiment of the present invention, sensor 90 is constructed substantially as described above except that active layer 96 is substantially free of a catalytically active enzyme such as lactate oxidase (i.e., layer 96 does not include more than about 0.01% by weight of a material which is catalytically active toward the analyte to be measured). Instead, according to this embodiment, layer 96 includes a catalytically non-active material such as bovine albumin serum. For this embodiment, layer 96 is formed in substantially the same fashion as the bovine albumin containing layer of correcting electrode 92 (described above). Hence, in this embodiment, the only source of catalysts (e.g., lactate oxidase) in sensor 90 is enzyme/polymer layer 99. For this embodiment, layer 99 preferably includes lactate oxidase.

The present invention will be further illustrated by the following examples which are intended to be illustrative in nature and are not to be construed as limiting the scope of the invention.

EXAMPLE 1

The electrically insulating substrate layer was formed from about 96% alumina and about 4% glass binder, available from Coors Ceramic Company, Grand Junction, Colo. The electrode layer was applied to the substrate layer as a 10 micrometer emulsion of high purity platinum paste, available as product number PC10208 from Metech, via screen printing with a 325 mesh stainless steel screen. A BTU zone furnace with a three zone dryer, from Fast Fire of Billerica, Mass., was used in firing the platinum emulsion. Firing was carried out per the manufacturer's recommendations, and the temperature was ramped to 750° C. for a thirteen minute peak.

The dielectric layer was screen printed as a 15 micrometer emulsion over portions of the substrate layer not covered by the electrode layer using a 325 mesh stainless steel screen. The material used for the dielectric layer was product number 9615 from duPont Electronics, Wilmington, Del. Subsequent to application on the substrate layer, the dielectric layer was fired at 750° C. for a ten minute peak.

An immobilized enzyme layer was deposited on the electrode layer using a thick screen printing method. The immobilized enzyme layer comprised a catalytically active quantity of lactate oxidase, available from Genzyme, Cambridge, Mass., as catalog number 1381, immobilized onto platinized carbon powder particles, available from E-TEK, Inc., Framingham, Mass.

An aqueous solution of APTES was made by pipetting about 1 gram of APTES (product number A0750, United Chemical Technolgies, Bristol, Pa.) into a container and adding about 19 grams of deionized water. This mixture was capped, shaken and allowed to stand for about five minutes. The dielectric and immobilized enzyme layers were then flooded with APTES solution and allowed to react for about ninety seconds. Excess solution was drained after this time period, and the sensor was spun on an Integrated Technologies spin coater at about 4000 revolutions per minute for about ninety seconds. The solution was then dried at room temperature and less than about 60% relative humidity for about 24 hours to form the hydrophobic layer.

The enzyme polymer layer was prepared as follows. First, a slurry of about 0.7 grams of PVOH in about 9.3 grams of deionized water by mixing the liquids at room temperature. The PVOH was about 99.9% hydrolyzed PVOH having an average molecular weight of from about 89,000 to about 98,000 (product number 34,158-4, Aldrich, Milwaukee, Wis.). The slurry was boiled to dissolve the PVOH and then cooled to room temperature. About 2 grams of this PVOH solution was added to about 0.08 grams of lactate oxidase (catalog number 1381, Genzyme, Cambridge, Mass.) at room temperature, and the lactate oxidase was dissolved by gently rolling by the container by hand.

This solution was applied to the hydrophobic layer using a spotting workstation which comprised a modified wire bonder (part number 827, Mech-El Industries, Woburn, Mass.) from which the ultrasonic box was disconnected, and the wire clamp, capillary, spool and chuck heater were removed. The wire capillary was replaced with a collet that mounts the dispensing needle (described below) to provide a manual pick and place mechanism, and a set of shelves was mounted on the right side of the workstation to support the syringe pump. The workstation included a microscope, a syringe pump (part number 74900, Cole Palmer Instrument Co., Niles, Ill.), a fifty microliter dispensing syringe (part number 1705, Hamilton), a one milliliter filler syringe (Moject) and a dispensing needle (part number Blunt-26G-7/16, Popper and Sons, New Hyde Park, N.Y.). Female Luer lock fittings (part number 20055, Alltech, Deerfield, Ill.) were used to connect the dispensing syringe and the filler syringe to a three way valve (part number 86727, Alltech). A PEEK ferrule (part number 20114, Alltech) joined PEEK compression fitting (part number 20124, Alltech) to the three way valve and to about twelve inches of 0.31 inner diameter PEEK tubing (part number 35710, Alltech). The PEEK tubing was connected to a PEEK ferrule (part number 20114, Alltech) and PEEK compression fitting which was connected to a PEEK union fitting (part number 20088, Alltech). A male Luer lock fitting (part number 90044, Alltech) connected the PEEK union fitting to the dispensing needle. The syringe pump was in communication with a footswitch such that depression of the footswitch resulted in dispensation of solution from the dispensing needle. The microscope was positioned adjacent the dispensing needle such that, when an aliquot of a solution was dispensed from the dispensing needle onto a surface (discussed below), the resulting surface could be observed through the microscope.

A portion of the lactate oxidase/PVOH solution was disposed within the syringe pump, and the dispensing needle was positioned adjacent the hydrophobic layer in an area above the immobilized enzyme layer. The foot pedal was tapped to dispense an aliquot of about 0.02 microliters of the solution onto the hydrophobic layer such that the solution covered an area of from about 60% to about 90% of the area of the immobized enzyme layer.

The membrane layer was prepared as follows. First, a surfactant solution was formed by disposing about 18 grams of distilled water in a container and 2 grams of Brij® 700 (ICI Specialty Chemicals, Wilmington Del.) was added to the water. This mixture was, shaken by hand and gently heated (warm but not hot to the touch) while being gently stirred with a stir bar for about thirty minutes. Next, the polymeric material was prepared by placing about 200 grams of an anionically stabilized, water-based hydroxyl endblocked polydimethylsiloxane elastomer, comprising by weight about 14% colloidal silica, commercially available as Fabric Coating FC-61 from Dow Corning was placed within a container. The FC-61 was then mixed with a laboratory mixer or rolled with ajar roller. About 200 grams of FC-61 was placed to a different, clean container, and about 10 grams of the Brij® 700 solution was added to the container. (It is to be noted the surfactant solution of Brij® 700 is added in amount about 0.5 times the weight of the FC-61). This mixture was mixed with a laboratory mixer to form the membrane material. An IVEK laboratory pump and an Integrated Technologies P-6000 spin coater was activated to a speed of about 7000 revolutions per minute. The first layer was formed by complete flooding of the wafer with the membrane material. When spinning was completed, the first layer was allowed to dry at room temperature for about fifteen minutes. Three additional layers of membrane material were sequentially added using a spin/flood/dry cycle. After all four layers were cast, the membrane material was cured for about twelve hours in a dust-free environment. The thickness of the membrane layer was about twenty micrometers.

Figure 13:
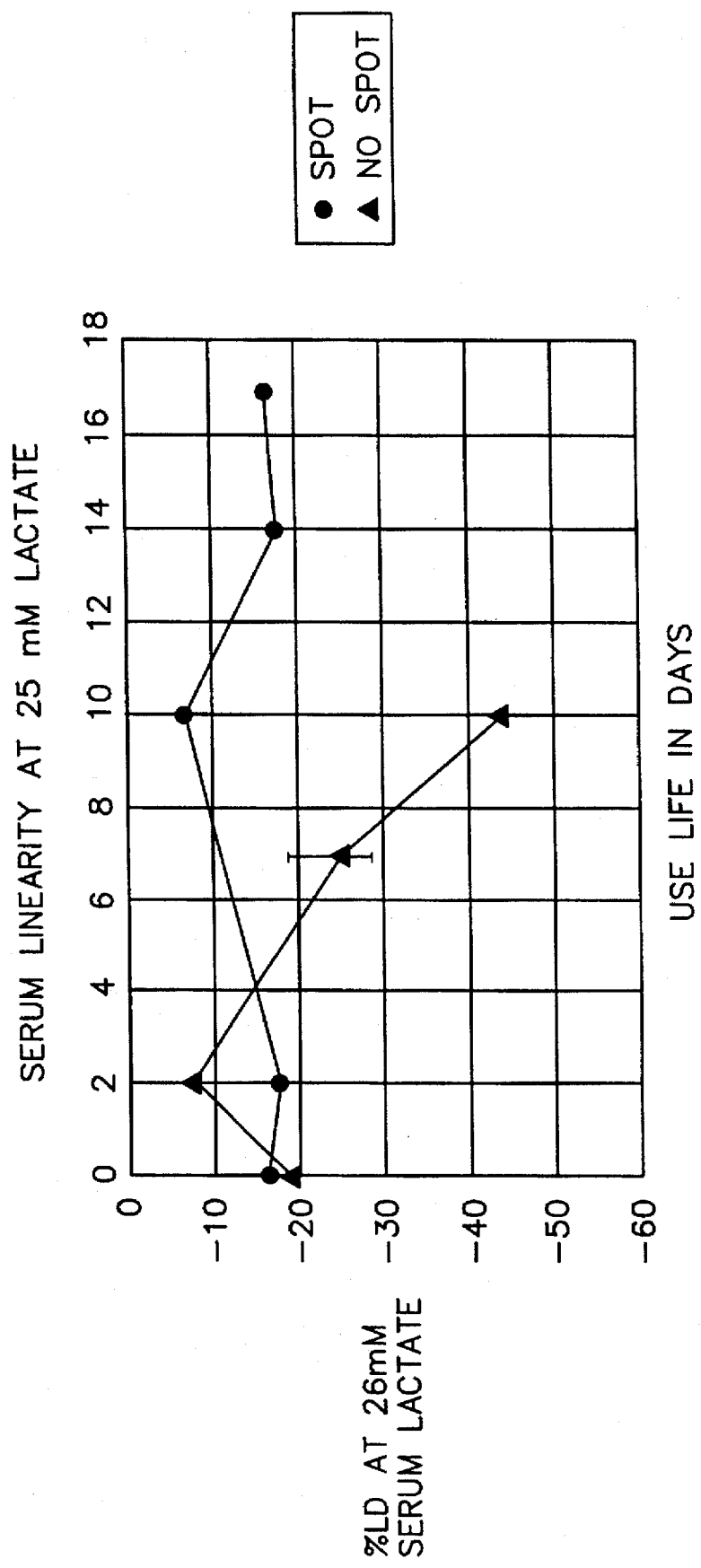
FIG. 13 is a graphical representation comparing the percentage linearity deviation between a sensor according to the present invention and a prior art sensor.

FIG. 13 shows the average percentage linearity deviation (% LD) of four sensors prepared according to this procedure as a function of time for an analyte solution of 25 mM lactate in serum. These sensors were hydrated and exposed to Ciba Corning Diagnostics 800 Series™ calibrating solutions and one hundred serum samples per day on a home built test station called the Sensorlab Life Cycler. The sensors were transferred to a Multichannel Electrochemical System (MES) test fixture and the performance evaluated after two hours, two days, seven days, ten days, fourteen days and seventeen days. Evaluation included measuring the linearity of the test solutions against a 25 mM aqueous solution of imidazole buffered lactate solutions.

The percent linearity deviation is a measure of the accuracy of the sensor at a particular lactate level and is calculated from the slope and intercept (calculated from the least squares regression of the output measured from 0 mM to 4 mM lactate) and the theoretical value (calculated from the measured slope time the lactate concentration as tested) at a particular test level. In other words, the percent linearity deviation is the theoretical output minus the actual output at a particular lactate concentration divided by the theoretical output times one hundred. A linear sensor has a percent linearity deviation of zero. Output that is lower than theoretical has a negative linearity. The change in linearity is also used, and is the difference between the percent linearity deviation and the percent linearity deviation at any given test point. Sensors having relatively poor linearity show negative changes in percent linearity deviation.

EXAMPLE 2

A sensor was constructed as in Example 1 with the exception that the hydrophobic layer and enzyme/polymer layer were not included (i.e., the membrane layer was applied directly to the immobilized enzyme layer and the dielectric layer). The corresponding results for the percentage linearity deviation are shown in FIG. 13. These experiments were performed as described in Example 1.

Having described certain embodiments of the present invention have been described herein, various alterations, modifications and improvements will readily occur to those skilled in the art. Such alterations, modifications and improvements are intended to be within the spirit and scope of the invention. The materials employed, as well as their shapes and dimensions, may be any required to provide the advantageous features of the invention as described herein. Moreover, while the present invention has been described as sensor including a plurality of electrodes, the invention is not limited to this configuration. Each element of the sensor may be used individually or in various combinations. Accordingly, the foregoing description is by way of example only and is not intended as limiting. The invention is limited only as defined in the following claims and the equivalents thereto.

What is claimed is:

1. A sensor for measuring a concentration of an analyte in a solution, comprising:
   a substrate layer formed from an electrically insulating material;
   an electrode layer formed from an electrically conductive material, the electrode layer being supported by the substrate layer;
   an immobilized enzyme layer including an enzyme immobilized in a support material, the immobilized enzyme layer being supported by the electrode, the immobilized enzyme layer electrode layer having a hydrophobicity; and
   a hydrophobic layer supported by the immobilized enzyme layer and the substrate layer, the hydrophobic layer having a hydrophobicity greater than the hydrophobicity of the immobilized enzyme layer, the hydrophobic layer having a water droplet advancing angle of from about 60° to about 100°.

2. A sensor in accordance with claim 1, wherein the immobilized enzyme layer has a water droplet advancing angle of from about 0° to about 20°.

3. A sensor in accordance with claim 2, wherein the water droplet advancing angle of the hydrophobic layer is from about 90° to about 100°.

4. A sensor in accordance with claim 1, wherein the water droplet advancing angle of the hydrophobic layer is from about 90° to about 100°.

5. A sensor in accordance with claim 1, wherein the immobilized enzyme layer includes lactate oxidase.

6. A sensor in accordance with claim 1, further comprising an enzyme-polymer layer including an enzyme, the enzyme-polymer layer being supported by the hydrophobic layer.

7. A sensor in accordance with claim 6, wherein the enzyme of the enzyme-polymer layer is lactate oxidase.

8. A sensor in accordance with claim 6, wherein the enzyme-polymer layer further includes a polymeric material.

9. A sensor in accordance with claim 8, wherein the polymeric material of the enzyme-polymer layer assists in maintaining a natural conformation of the second enzyme.

10. A sensor in accordance with claim 8, wherein the polymeric material of the enzyme-polymer layer is a polyvinyl alcohol.

11. A sensor in accordance with claim 1, further comprising at least one membrane layer including a polymeric material.

12. A sensor in accordance with claim 11, wherein the at least one membrane layer includes a plurality of membrane layers.

13. A sensor in accordance with claim 11, wherein the at least one membrane layer further includes a surfactant.

14. A sensor in accordance with claim 13, wherein the surfactant is a nonionic surfactant.

15. A sensor in accordance with claim 13, wherein the surfactant includes a hydrophobic hydrocarbon chain bonded to an oligoalkylene oxide.

16. A sensor in accordance with claim 1, wherein the immobilized enzyme layer is substantially free of a catalytically active enzyme.

17. A sensor in accordance with claim 16, further comprising an enzyme-polymer layer including an enzyme.

18. A sensor in accordance with claim 17, wherein the enzyme-polymer layer is supported by the hydrophobic layer.

19. A sensor in accordance with claim 17, wherein the enzyme of the enzyme-polymer layer is lactate oxidase.

20. A sensor in accordance with claim 17, wherein the enzyme-polymer layer further includes a polymeric material.

21. A sensor in accordance with claim 20, wherein the polymeric material of the enzyme-polymer layer assists in maintaining a natural conformation of the second enzyme.

22. A sensor in accordance with claim 20, wherein the polymeric material of the enzyme-polymer layer is a polyvinyl alcohol.

23. A sensor in accordance with claim 16, further comprising at least one membrane layer including a polymeric material, the at least one outer layer being supported by the enzyme-polymer layer.

24. A sensor in accordance with claim 23, wherein the at least one membrane layer includes a plurality of membrane layers.

25. A sensor in accordance with claim 23, wherein the at least one membrane layer further includes a surfactant.

26. A sensor in accordance with claim 25, wherein the surfactant is a nonionic surfactant.

27. A sensor in accordance with claim 25, wherein the surfactant includes a hydrophobic hydrocarbon chain bonded to an oligoalkylene oxide.

28. A sensor in accordance with claim 1, wherein the hydrophobic layer includes a silane.

29. A sensor in accordance with claim 1, wherein the hydrophobic layer includes an aminosilane.

30. A sensor in accordance with claim 1, wherein the hydrophobic layer includes aminopropyltriethoxysilane.

31. A method of making a sensor for measuring a concentration of an analyte in a solution, the method comprising the steps of:

providing a substrate layer;

disposing an electrically conductive layer along a surface of the substrate layer to form an electrode layer;

disposing a layer including an enzyme immobilized in a support material along a surface of the electrode layer to form an immobilized enzyme layer; and disposing a hydrophobic layer formed from a silane along a surface of the immobilized enzyme layer.

32. A method in accordance with claim 31, wherein the steps of disposing the hydrophobic layer include the steps of:

pouring a silane solution onto the surface of the immobilized enzyme layer;

draining a portion of the silane solution; and removing excess silane solution by spinning the sensor with a spin coating device.

33. A method in accordance with claim 32, further comprising a step of disposing an enzyme-polymer layer along a surface of the hydrophobic layer.

34. A method in accordance with claim 33, wherein the step of disposing the enzyme-polymer layer includes the steps of:

forming a slurry of a polymer and water;

heating the slurry to dissolve the polymer in the water to form a polymer solution;

cooling the polymer solution; and adding an enzyme to the polymer solution to form an enzyme solution.

35. A method in accordance with claim 34, wherein the step of disposing the enzyme-polymer layer includes the step of disposing the enzyme solution along the hydrophobic layer with a spotting workstation.

36. A method in accordance with claim 35, further comprising the steps of:

disposing a membrane layer along a surface of the enzyme-polymer layer; and disposing the membrane layer along a surface of the hydrophobic layer.

37. A method in accordance with claim 36, wherein the steps of disposing the membrane layer include the steps of:

flooding the surface of the enzyme-polymer layer with a first portion of a membrane solution including a polymeric material and a surfactant; and removing excess membrane solution by spinning the sensor with a spin coating apparatus to form a first membrane layer.

38. A method in accordance with claim 37, further comprising the steps of:

disposing a second portion of the membrane solution along a surface of the first membrane layer; and removing excess membrane solution by spinning the sensor with a spin coating apparatus.

39. In a sensor for measuring a concentration of an analyte in a solution, the sensor being formed from a substrate layer, an electrode layer and an immobilized enzyme layer having a hydrophobicity, the electrode layer being disposed on the substrate layer, the immobilized enzyme layer being disposed on the electrode layer, wherein the improvement comprises:

a hydrophobic layer having a hydrophobicity greater than the hydrophobicity of the immobilized enzyme layer, the hydrophobic layer being supported by the immobilized enzyme layer, the hydrophobic layer having a water droplet advancing angle of from about 60° to about 100°.

40. A sensor in accordance with claim 39, wherein the immobilized enzyme layer includes an enzyme.

41. A sensor in accordance with claim 39, wherein the immobilized enzyme layer is substantially free of a catalytically active enzyme.

42. A sensor in accordance with claim 39, wherein the hydrophobic layer is formed from aminopropyltriethoxysilane.

43. A sensor in accordance with claim 39, further comprising an enzyme-polymer layer including an enzyme, the enzyme containing layer being supported by the hydrophobic layer.

44. A sensor in accordance with claim 43, wherein the enzyme-polymer layer further includes a polymeric material.

45. A sensor in accordance with claim 39, further comprising at least one membrane layer including a polymeric material.

46. A sensor in accordance with claim 45, wherein the membrane layer further includes a surfactant.

47. A sensor in accordance with claim 39, wherein the hydrophobic layer includes a silane.

48. A sensor in accordance with claim 39, wherein the hydrophobic layer includes an aminosilane.

49. A sensor for measuring a concentration of an analyte in a solution, the sensor comprising:
    a substrate layer formed from an electrically insulating material;
    an electrode layer formed from an electrically conductive material, the electrode layer being supported by the substrate layer;
    an immobilized enzyme layer including an enzyme immobilized in a support member, the immobilized enzyme layer being supported by the electrode layer;
    an enzyme-polymer layer including an enzyme, the enzyme-polymer layer being disposed above the immobilized enzyme layer; and
    an hydrophobic layer disposed between the immobilized enzyme layer and the enzyme-polymer layer, the hydrophobic layer being formed from a silane.

50. A sensor in accordance with claim 49, wherein the hydrophobic layer is formed from an aminopropylsilane.

51. A sensor in accordance with claim 50, further comprising an inactive electrode uncovered by the enzyme-polymer layer.

52. A sensor in accordance with claim 50, wherein the hydrophobic layer has a water droplet advancing angle of from about 60° to about 100°.

53. A sensor in accordance with claim 50, wherein the hydrophobic layer is formed from aminopropyltriethoxysilane.

54. A sensor in accordance with claim 49, wherein the hydrophobic layer has a water droplet advancing angle of from about 90° to about 100°.

55. A sensor in accordance with claim 54, wherein the immobilized enzyme layer has a water droplet advancing angle of from about 0° to about 20°.

56. A sensor in accordance with claim 54, wherein the immobilized enzyme layer has a water droplet advancing angle of from about 0° to about 20°.

57. A sensor in accordance with claim 49, wherein the enzyme of the immobilized enzyme layer is lactate oxidase.

58. A sensor in accordance with claim 57, wherein the enzyme of the enzyme-polymer layer is lactate oxidase.

59. A sensor in accordance with claim 49, wherein the enzyme of the enzyme-polymer layer is lactate oxidase.

60. A sensor in accordance with claim 49, wherein the enzyme-polymer layer further comprises a polymer.

61. A sensor in accordance with claim 60, wherein the polymer of the enzyme-polymer layer is capable of assisting in maintaining a natural conformation of the enzyme of the enzyme-polymer layer.

62. A sensor in accordance with claim 60, wherein the polymer of the enzyme-polymer layer is a polyhydric alcohol.

63. A sensor in accordance with claim 49, further comprising a hydrophobic layer disposed between the immobilized enzyme layer and the enzyme-polymer layer, the hydrophobic layer being formed from aminopropyltriethoxysilane, wherein the substrate layer is formed from alumina, the electrode layer is formed from platinum, the immobilized enzyme layer includes lactate oxidase and the enzyme polymer layer includes lactate oxidase.

64. In a sensor for measuring a concentration of an analyte in a solution, the sensor being formed from a substrate layer, a dielectric layer, an electrode layer and an immobilized enzyme layer, wherein the electrode layer is disposed on the substrate layer, the dielectric layer is disposed on the substrate, and the immobilized enzyme layer is disposed on the electrode layer, and wherein the improvement comprises:
    an enzyme-polymer layer including an enzyme, the enzyme-polymer layer being disposed above the immobilized enzyme layer and a hydrophobic layer disposed between the immobilized enzyme layer and the enzyme-polymer layer, the hydrophobic layer being formed from a silane.

65. A sensor in accordance with claim 64, wherein the enzyme layer of the enzyme-polymer layer is lactate oxidase.

66. A sensor in accordance with claim 64, wherein the enzyme-polymer layer further includes a polymer.

67. A sensor in accordance with claim 64, wherein the enzyme-polymer layer further includes a polymer.

68. A sensor in accordance with claim 67, wherein the polymer of the enzyme-polymer layer assists in maintaining a natural conformation of the enzyme of the enzyme-polymer layer.

69. A sensor in accordance with claim 67, wherein the polymer of the enzyme-polymer layer is a polyhydric alcohol.

70. A sensor in accordance with claim 67, wherein the polymer of the enzyme-polymer layer is a polyvinyl alcohol.

71. A sensor in accordance with claim 64, wherein the hydrophobic layer includes an aminosilane.

72. A sensor in accordance with claim 64, wherein the hydrophobic layer includes aminopropyltriethoxysilane.

* * * * *